US006249700B1

United States Patent
Alt

(12) United States Patent
(10) Patent No.: US 6,249,700 B1
(45) Date of Patent: Jun. 19, 2001

(54) DEFIBRILLATOR WITH IMPROVED HEMODYNAMIC RESPONSE AND ENHANCED MYOCARDIAL STABILITY

(76) Inventor: Eckhard Alt, Eichendorffstrasse 52, Ottobrunn (DE), 85521

( * ) Notice: Subject to any disclaimer, the term of this patent is extended or adjusted under 35 U.S.C. 154(b) by 0 days.

(21) Appl. No.: 09/449,444

(22) Filed: Nov. 25, 1999

Related U.S. Application Data

(63) Continuation-in-part of application No. 08/874,032, filed on Jun. 12, 1997, now Pat. No. 6,096,061.

(51) Int. Cl.[7] ................................................. A61N 1/365
(52) U.S. Cl. ..................................... 607/4; 607/19
(58) Field of Search ............................. 607/4, 6, 17, 19, 607/21, 24, 25

(56) References Cited

U.S. PATENT DOCUMENTS

| | | |
|---|---|---|
| 4,782,836 | 11/1988 | Alt . |
| 4,846,195 | 7/1989 | Alt . |
| 4,926,863 | 5/1990 | Alt . |
| 5,014,700 | 5/1991 | Alt . |
| 5,031,615 | 7/1991 | Alt . |
| 5,065,759 | 11/1991 | Begemann et al. . |
| 5,334,222 | 8/1994 | Salo et al. . |
| 5,342,404 | 8/1994 | Alt et al. . |
| 5,360,436 | 11/1994 | Alt et al. . |
| 5,370,667 | 12/1994 | Alt . |
| 5,423,869 | 6/1995 | Poore et al. . |
| 6,096,061 | * 8/2000 | Alt et al. ................................. 607/4 |

FOREIGN PATENT DOCUMENTS

| | | |
|---|---|---|
| 0 249 820 | 2/1988 | (EP) . |
| 0 580 128 | 1/1994 | (EP) . |
| 0 616 819 | 9/1994 | (EP) . |
| 0 702 980 | 3/1996 | (EP) . |

* cited by examiner

Primary Examiner—Jeffrey R. Jastrzab
(74) Attorney, Agent, or Firm—Blank Rome Comisky & McCauley LLP

(57) ABSTRACT

An implanted defibrillator provides a device-implemented method of delivering cardiac pacing, cardioversion and defibrillation therapies in selective response to dysrhythmia detection of an implant patient's cardiac signal. The patient's heart rate is sensed, and cardioversion/defibrillation therapies are delivered by the device by producing electrical shocks of adjustable energy level for application to the patient's heart in response to applicable detected levels of pathologic accelerated heart rate. A match between the generated cardiac pacing rate and the contemporaneous hemodynamic needs of the implant patient under conditions of rest and physical activity is optimized by sensing periods of patient physical activity and rest and generating a signal representative thereof to control the cardiac pacing rate accordingly and according to the extent of activity by means of an accelerometer mounted on hybrid electronic circuitry of the device. The pacing rate is optimized by confirmation or no confirmation from the output signal of the accelerometer with a second, complementary sensor electrically coupled to electronic circuitry of the defibrillator.

24 Claims, 1 Drawing Sheet

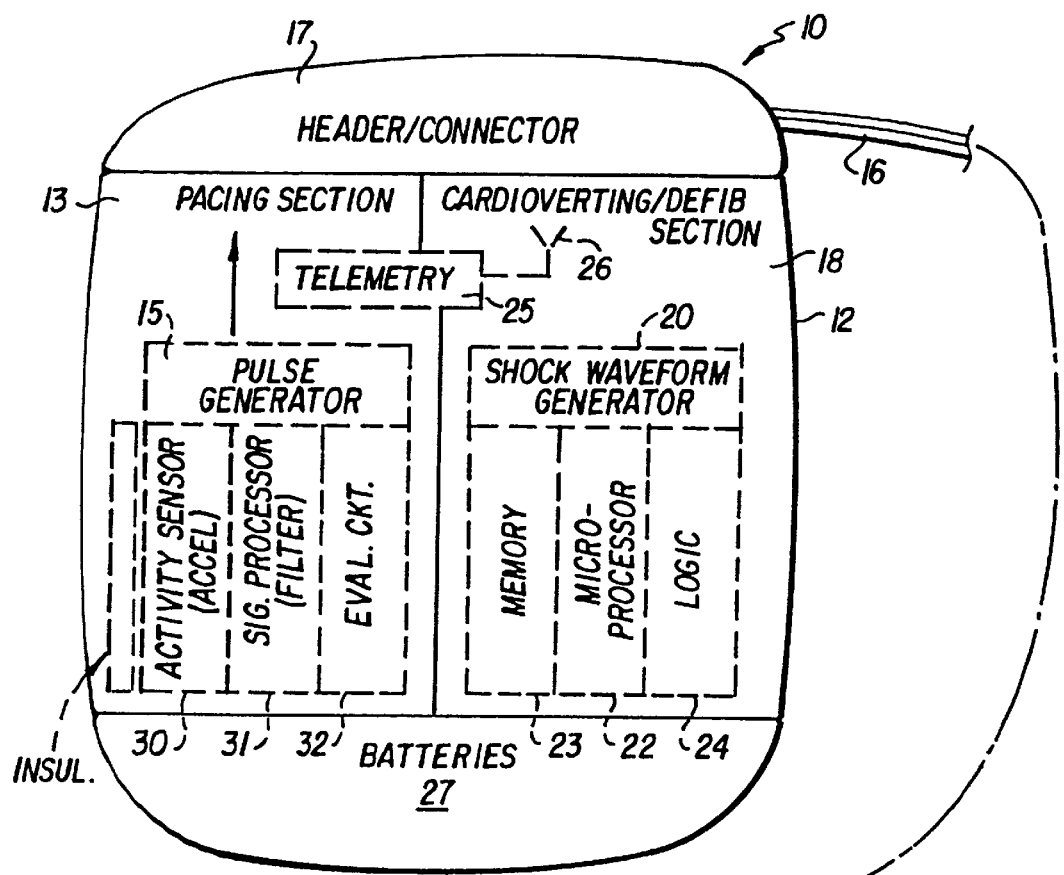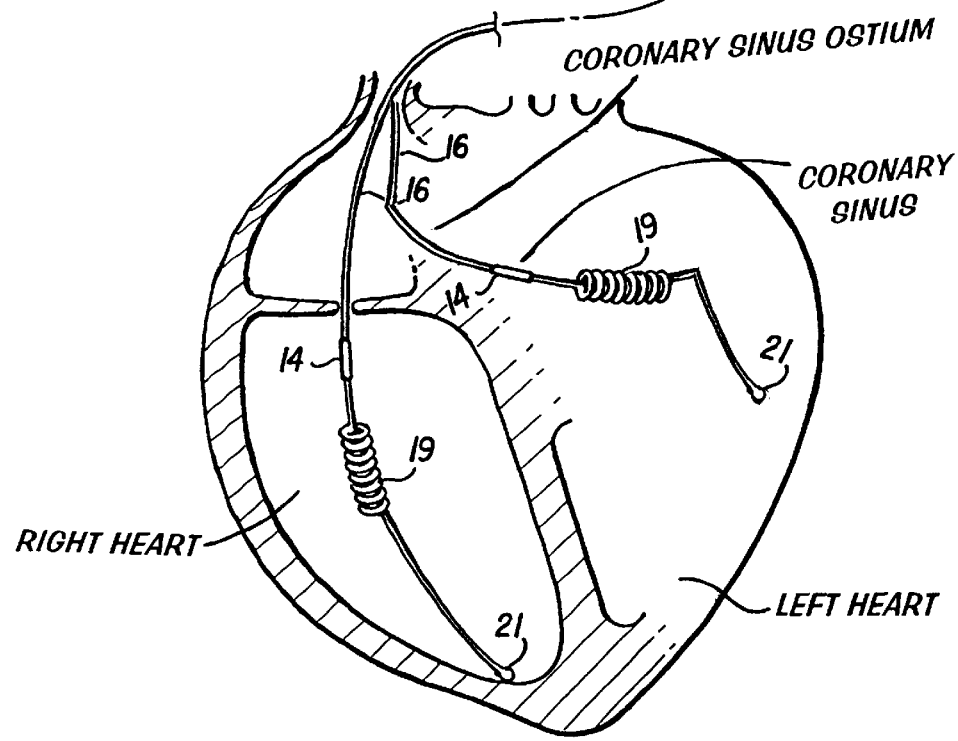

DEFIBRILLATOR WITH IMPROVED HEMODYNAMIC RESPONSE AND ENHANCED MYOCARDIAL STABILITY

CROSS-REFERENCE TO RELATED APPLICATIONS

This application is a continuation-in-part of application Ser. No. 08/874,032, filed Jun. 12, 1997, in the name of the same applicant now U.S. Pat. No. 6,096,061.

BACKGROUND OF THE INVENTION

The present invention relates generally to implantable medical interventional devices which provide a range of pacing, cardioversion, and defibrillating functions to preserve the life and stamina of the patient, and more particularly to an implantable defibrillator that exhibits improved hemodynamic response and enhanced myocardial stability to vastly improve the quality of life of the patient. As used herein, the terminology "implantable defibrillator" is intended to refer broadly to a device which is adapted to perform a variety of essential cardiac interventional functions, as is typically the case in actual medical device practice, and not merely limited to defibrillation therapy.

Administering therapy from implantable defibrillators has proven to be highly effective in preventing sudden cardiac death. Nonetheless, many patients provided with defibrillators suffer from myocardial failure attributable to serious underlying disease that contributes to electrical instability and reduced myocardial function. The determinants of cardiac output (the volume of blood discharged from the ventricle per minute), especially during exercise, are volume (the volume of blood discharged from the ventricle with each contraction) and heart rate (cardiac output=stroke volume×heart rate). While the normal heart is capable of increasing its stroke volume by a factor of 50% when the patient goes from conditions of rest to exercise, the majority of patients who are candidates for an implantable defibrillator lack that degree of contractile reserve. For such patients it is essential that the implanted device adapt the heart rate to closely if not precisely match the limited cardiac output to the needs of the patient's body.

While a healthy person or a patient who may be only slightly myocardially compromised has mechanisms that enable his or her cardiac output to adapt to a wider variation of stroke volume, the typical defibrillator patient lacks any such mechanism by which to adapt, and instead predominantly adjusts cardiac output by means of a modification of heart rate. But if the patient's heart rate is too low for a given exercise load, an increase in endiastolic left ventricular filling pressure is experienced. In essence, the heart is simply incapable on its own of pumping sufficient blood into systemic circulation, which results in congestion of the pulmonary system and reduced oxygen pressure, and also affects the stability of the myocardium. Increased endiastolic pressures cause an increased stress to the myocardial wall which is a factor in the triggering of ventricular extrasystoly (i.e., premature ventricular contraction or PVC). Although the malady is commonly experienced in otherwise relatively healthy adults who engage in heavy smoking or experience severe emotional excitement, it is most often encountered to be of multifocal origin in cases of organic heart disease or digitalis intoxication, and can lead to ventricular tachycardia, and ultimately, ventricular fibrillation.

In the past, a wide variety of sensors has been proposed for potential control of ventricular rate. But not all of the potential sensor signals are suitable for heart rate control in patients needing an implantable defibrillator. Control that produces a heart rate which is either too slow or too fast in terms of the patient's metabolism, is inappropriate. A sensor that produces these types of improper responses, for example because of its sensitivity to environmental noise sources or to other phenomena which are not matched to the body metabolism, is unsuitable for use in implantable defibrillators or other cardiac interventional devices.

It is therefore a principal aim of the present invention to provide an implantable defibrillator with improved hemodynamic response, and which provides greater myocardial stability. The desire is to achieve these results by use in the medical interventional device of a particularly suitable and effective rate control signal, so that the frequency of device intervention by delivery of either cardioverting or defibrillating shocks will be substantially reduced. Ultimately, although the device is intentionally implemented to deliver such therapy repeatedly despite its battery-operated nature, a marked reduction in the number of times the patient will receive shocks from the device by virtue of a more circumspect hemodynamic response of the device will substantially lessen duress on the patient's myocardial function and other aspects of his physiology, including orthopedic distress, for example, and with it, considerably less pain and general discomfort to the patient. Furthermore, reducing the number of shocks that must be generated by the device is effective to conserve energy and will thereby prolong the useful life of the device. A more appropriate rate control can also serve to increase the patient's capacity for exercise, and with it, improve the patient's quality of life.

SUMMARY OF THE INVENTION

The present invention provides means for limiting the tendency of a diseased heart to undergo pathologic increases in heart rate—such as extrasystole, reentrant tachycardia, and so forth—so that less need will exist for treating accelerated heart rate by means of debilitating shocks to the patient's heart. With this emphasis on what might be termed prevention rather than cure, not only will the patient experience less injury to cardiac and other body tissue, but battery life of the implanted device will increase and the frequency of subjecting the patient to surgical procedures for device replacement will decrease. Since state of the art automatic implantable cardioverter/defibrillators (sometimes referred to in short as "AICDs" or "ICDs") possess the capability to provide all of the conventional pacing functions as well as to provide the therapies necessary for antitachycardia, cardioversion and defibrillation, the potential of fered by the pacing function is conveniently examined in the effort to reduce dependence on cardioverting and defibrillating functions of the device.

Another aspect of the invention is to prolong the battery life of the device by reducing the pacing rate at prolonged resting periods such as during nighttime hours. While a low pacing rate such as 40 or 50 beats per minute (bpm) certainly is too low to provide adequate hemodynamics during daytime hours with activity, the accelerometer or other sensor controlled rate adaptation allows therefore an adequate increase with physical or emotional exercise. The in pacing rate can be either linked to a clock function inside the device or adjusted to periods of activity or inactivity detected by the sensor. In case of prolonged periods of inactivity and clearly identified periods of activity, the device can define day and night phases over the course of a certain time window. A combination of the clock function and sensed activity or rest is used to refine the pacing rate including further reducing it in those prolonged periods of inactivity.

In one of its aspects the present invention seeks to optimize a match between the pacing functions of the implanted device and the patient's metabolism. By achieving a better match of the pacing function to the heart rate of a normal healthy subject, within all of environmental conditions the patient is likely to encounter in the pursuit of a healthy lifestyle, the cardiac function will be improved in at least two critical ways. First, matching decreases endiastolic filling pressure to reduce the chances of intrinsic rhythm disorders by reducing the stress factors, and second, matching operates to prevent extrasystoly by overdrive suppression. Overdrive suppression may be used when the patient suffers a pathologic ventricular tachycardia, for the purpose of establishing a heart rate that exceeds the resting heart rate by, say 10 to 40 bpm. This shortens the Q-T interval and the ventricle's refractory period. The goal is to prevent ventricular ectopy (i.e., an aberrant impulse that has its origin in an abnormal focus) that frequently starts at a relatively low intrinsic heart rate, and may not occur at a substantially higher heart rate. Using an implanted pacemaker to increase the heart rate enables the establishment of a dominant rhythm to prevent ectopic or reentrant ventricular beats.

The implantable defibrillator employs rate responsive pacing in general and an accelerometer-based therapy in particular to achieve the function of matching the pacing rate to the patient's metabolic needs. The use of rate responsive or rate adaptive pacing or sensors typically associated with detecting patient exercise or activity alone does not solve the problem of an adequate response behavior. Some prior art sensors are no more than laboratory curiosities, either requiring complex mechanisms to provide the necessary indicia or complicated implant procedures, or both, which makes them cost prohibitive even aside from addressing their capability to provide the aforesaid close or precise matching. Other sensors suffer from insufficient sensitivity, and inadequate response at the commencement and completion of exercise or activity—such as those that sense body temperature (e.g., central venous blood temperature) or respiratory rate (e.g., minute ventilation). Still others which may be useful strictly for activity sensing as opposed to exercise sensing—the difference being response to body movement or motion in contrast to response to body workload—tend to be insensitive to the level of work being performed.

In contrast, accelerometer-based activity sensors provide faithful response to the body's true metabolic and hemodynamic needs under conditions of rest and exercise, and the accelerometer is the preferred sensor for the matching function performed by the present invention. According to the invention, an implantable defibrillator implemented to perform defibrillation and cardioversion therapy and pacing functions as well, is provided with an accelerometer to detect patient activity and true physical exercise so that the pacing rate is matched to the metabolic and hemodynamic needs of the implant patient. A variable baseline pacing rate is used to assure that the rate accurately reflects current conditions of patient rest and exercise, with rate control based on the output signal of the accelerometer. The output signal preferably is processed to enhance its sensitivity and specificity for recognition of body movement signals that correlate with physical exercise of the patient, and to reject those signal components that fail to so correlate. The output signal of the accelerometer is enhanced by narrow bandpass filtering of the sensor signal in a range between 0.1 Hz and 10.0 Hz as the corner frequencies.

In a preferred embodiment, the sensor is mounted onto hybrid electronic circuitry together with other components such as capacitors, resistors and a semiconductor processor which may be mounted in the case that houses the defibrillator. External interference is eliminated or substantially reduced by avoiding sensitivity of the sensor to pressure on the case, such as by mechanically isolating the activity sensor from the case. In addition, the use of a miniaturized accelerometer adds little to the total complexity and size of the hybrid.

To confirm the condition of patient exercise or rest indicated by the accelerometer, a second, complementary sensor is used for response to a parameter representative and an approximate measure of the metabolic and hemodynamic needs of the patient under conditions of rest and exercise. Suitable exemplary parameters include central venous blood temperature, minute ventilation, Q-T interval of the cardiac cycle, or intracardiac phenomena derived from a special sensing lead within the heart of the patient. The invention of sensor cross check representing a beneficial combination of sensors per se is described, for example, in applicant's U.S. Pat. Nos. (USPNs) 4,782,836 and 5,014,700, both of which are incorporated herein by reference in their entirety.

BRIEF DESCRIPTION OF THE DRAWINGS

The above and other objects, aspects, features and attendant advantages of the present invention will become apparent from a consideration of the following detailed description of the presently contemplated best mode of practicing the invention, with reference to certain preferred embodiments and methods thereof, taken in conjunction with the accompanying drawings, in which:

The sole FIGURE of drawing is a simplified block diagram of a defibrillator with pacing and cardioversion/defibrillation shock therapy functions, that uses an accelerometer sensor to provide enhanced discrimination of true exercise signals.

DETAILED DESCRIPTION OF A PREFERRED EMBODIMENT AND METHOD

Referring to the FIGURE, the implantable defibrillator 10 of the invention may incorporate conventional component parts to implement the various therapeutic functions of pacing, cardioversion, and defibrillation which it will be automatically called upon to provide in response to detection of respective dysrhythmias in the patient's cardiac activity. The defibrillator is not shown to scale relative to the size of the patient's heart depicted in the drawing. Substantially all components of the defibrillator 10 are housed in a hermetically sealed case 12 which is biocompatible to avoid an adverse reaction to contact with body tissue and fluids. A complementary sensor 14 and cardiac leads and associated electrodes are coupled to the circuitry internal to the defibrillator device by a connector 17 on a header of the housing or case 12. The broad range of functions of the implantable device are provided by a cardiac pacing section 13, with associated pulse generator 15; and a cardioverting and defibrillating section 18, with associated shock waveform generator 20.

The defibrillator 10 contains a microprocessor 22 and associated memory 23 and logic 24 which cooperate with each other and with the various therapy function sections to achieve programming, deliver and implement instructions and program information, and maintain compatibility between the functional components of the device. The logic circuitry performs functions such as sampling, comparing, and performing other functions in the device. A telemetry section 25 and associated antenna 26 permit communication between the implanted device and an external programmer or programming console (not shown). Battery section 27 has one or more conventional batteries adequate to supply electrical power to the various sections and components so that they may perform their respective functions in the device. The defibrillator may also include a conventional crystal controlled timer (not shown) to control the timing of the logic, microprocessor, and other components of the device, and a reed switch (not shown) to allow limited patient control of some of the device therapeutic functions, by use of an external magnet.

The defibrillator 10 further includes an activity sensor 30 that preferably comprises an accelerometer, together with signal processing circuitry 31 for processing signals indicative of the current status of physical activity or exercise (or rest) of the patient. External complementary sensor 14 may be of any suitable practical conventional type, such as a central venous blood temperature sensor in the form of a thermistor which is incorporated into a cardiac lead for placement in a chamber (e.g., the right ventricle) of the patient's heart when the lead is implanted. The latter sensor generates a signal representative of the patient's current blood temperature, and this signal is then processed to confirm or contest the accuracy of information derived from the activity sensor (accelerometer) 30. For purposes of processing the activity signal, processing circuit 31 incorporates a bandpass filter especially to reduce the response of the processing to signal frequencies exceeding 10 Hz. That is, the circuit's response drops off at those frequencies, as is discussed in greater detail below.

Activity sensor 30 is preferably housed within case 12 mounted on the hybrid, but may instead be disposed in a separate case (not shown) that is connected to the hybrid by electrical contacts. The activity sensor is mechanically isolated from the case by being mounted away from the internal surface of the case, or by use of suitable layers of non-conductive, mechanically insulating material, to avoid any effect on its output signal as a result of direct pressure on the case. The sensor is preferably an accelerometer of piezoelectric, piezoresistive or piezocapacitive type, adapted to generate an electrical signal having amplitude and frequency components representing accelerational forces on or movements by the patient. Preferably, the accelerometer or other activity sensor is mounted within the device (or even in a separate sealed housing outside the device) to detect acceleration in a predominantly anterior-posterior direction of movement of the patient. The accelerometer may be mounted along a horizontal axis on the defibrillator device. A suitable accelerometer version of an activity sensor is in applicant's U.S. Pat. No. (USPN) 5,031,615 ("the '615 patent"), which is incorporated herein by reference in its entirety.

The '615 patent contains a detailed description of an accelerometer sensor such as 30 and related processing circuitry such as 31, in which the accelerometer comprises a low power microminiature mechanoelectrical converter or transducer which is either configured to include, or has in the related processing circuit, a low pass filter to pass a frequency band below about 4 Hz. In one form described in the '615 patent, a suitable mechanoelectrical transducer activity sensor has an integrated signal filter circuit to provide the desired low-pass frequency band. A silicon monocrystalline substrate with a 1-0-0 orientation of crystal planes, a p+ epitaxial conductive layer formed on the surface thereof, and a polycrystalline silicon layer sandwiched between passivating layers of silicon dioxide, together form a structure in which a cavity is etched in the substrate to form a rectangular plate connected by four arms to the corners of the cavity. The suspended plate in that configuration is the element responsive to acceleration. An integrated circuit (IC) fabricated in the silicon layer can be used for processing the signal generated by movement of the rectangular plate on the arms, and, if the low pass filter is not integral with the semiconductor structure, a separate suitable filter circuit may be incorporated with the signal processing circuitry. For further details and a drawing of such a configuration for the activity sensor and related circuitry, the reader is referred to the '615 patent.

Alternatively, other forms of accelerometer-based activity sensors, such as a pair of mercury ball sensors of the type described in applicant's U.S. Pat. No. 4,846,195, also incorporated fully herein by reference, may be used rather than a sensor of the piezoelectric, piezocapacitive or piezoresistive type. Two mercury ball-type sensors are affixed together with a permanent orthogonal orientation relative to one another, so that the activity signal output of each sensor may be used to discriminate between physical activity types.

In U.S. Pat. No. 4,926,863 ("the '863 patent"), also incorporated in its entirety herein by reference, applicant teaches that a sensed activity signal should be limited to a frequency range below 10 Hz, and preferably to 4 Hz and below, to detect true physical exercise by the patient, and to discriminate against (i.e., distinguish from) other disturbances which are external or internal to the body. The maximum forces and the maximum signal amplitudes occurring with physical activity are in the frequency range of the individual's steps in walking or running. The amplitude of the motion signals in that frequency range far exceeds the amplitude of signals from respiration and heart beat.

In contrast, amplitude maxima in the higher-frequency range in, around, or greater than 10 Hz are more the result of sudden spasmodic movements which do not represent true metabolic exercise or activity. Noise external to the body such as operating machinery in close proximity, or arising from within the body such as from coughing, laughing, and sneezing, also displays amplitudes in the higher-frequency range which are up to about tenfold the amplitude of signals in the same range attributable to true physiologic exercise. The signals emanating from noise sources tend to swamp activity-induced signals at those higher frequencies. Moreover, even light pressure on the pacemaker, such as that attributable to jostling of the patient in a crowd, is picked up by the activity sensor to create interference in the higher-frequency range, but is detected with only very low amplitude in a low-frequency range up to about 10.0 Hz. Also, the duration of the pulse wave from propagation of the pulse with every heart beat is in a range of about 70 to 120 ms, which has an impulse characteristic with maximum amplitude at about 10 Hz, even though the heart rate itself is in the range from 60 to 180 beats per minute (bpm) corresponding to a frequency of 1 to 3 Hz. By limiting detection from the activity sensor to only the low-frequency content below about 10 Hz, correlation with the metabolic demand of the body in true exercise is considerably enhanced.

Activities such as riding in a car or on a bicycle on an uneven road surface causes considerably less interfering noise in the low-frequency range than in the higher-frequency range. In addition, use of the frequency spectrum below 4 Hz allows reliable detection of the amplitude maxima and minima with a relatively low sampling rate compared to the frequency range above 10 Hz, which saves energy and is a significant advantage for a battery-operated, implanted medical device.

Accordingly, use of the frequency band below about 4 Hz, along with establishing different baseline values as ongoing levels of comparison with changes in workload, as is also taught by the '863 patent, gives the accelerometer-based activity pacemaker the attributes of fast response and reliable pacing at a variable rate adapted to the level of physical exertion of the patient, closely corresponding to the heart rate of a normal healthy person under the same conditions of physical exertion.

It can be shown by Fourier analysis of the output signals of the accelerometer for different types of activity that the frequency spectrum of a walking patient exhibits a clear maximum amplitude at a frequency of about 2 Hz, with significantly declining signal amplitudes the range exceeding 4 Hz. An increase in the amplitude of the low-pass activity signal is observed with increasing exercise, as the patient goes from walking to running, with a decline in amplitude upon a return to walking and ultimately to a state of rest. Fourier analysis also demonstrates that the low-pass activity signal is virtually unencumbered by noise sources external or internal to the body, whereas the higher frequency range is sufficiently affected to cause the activity signal to be buried in the noise.

As described in applicant's U.S. Pat. No. 5,360,436 ("the '436 patent") which is also incorporated in its entirety by reference herein, an activity-sensing, rate-responsive pacemaker may be programmed to provide different response rates based on an algorithm or algorithmic curve representing the desired responses (heart rates) for different types of physical activity of the patient. Each type of activity is represented by a distinct and different curve or portion of a curve of heart rate or pacing rate versus acceleration force or signal amplitude, with a transition rate between the two or more portions. A family of such curves of physical activity versus pacing rate may be externally programmed for rate control. At low rates of detected acceleration for a particular workload, such as bicycling, the pacing rate is adjusted as appropriate for that activity. If the patient is walking or running, which produces higher detected accelerations for the same workload, the pacing rate is adjusted to fit the curve appropriate for that type of physical activity. In that way the patient experiences the proper heart rate for different types of activity involving the same workload.

Turning again to the sole FIGURE of drawing, the low-pass components of the activity signal are further processed after treatment by the signal processing circuit, using logic and memory circuits of the implantable defibrillator 10. The further processing is performed to select an algorithmic curve as the control signal for determining an appropriate rate of pacing pulses generated by pulse generator 15 under the control of conventional rate control circuitry thereof, according to the type of physical exercise in which the patient is engaged.

The output pulses of generator 15 are applied to connector 17 in the header of case 12, which is configured to accept the proximal end of a transvenous lead 16 which has a conductor and associated pacing electrode or electrodes 21 at its distal end to be positioned at the apex of the right ventricle or additionally within the coronary sinus for stimulation of the left heart as well or even the left heart alone, when threaded into place by the implanting physician, and which may also include a separate defibrillation/cardioversion coil 19 to be positioned, for example, in the right ventricle or coronary sinus when the lead is fully implanted. Electrode 21 is also used to sense intracardiac activity for use in assessing whether a dysrhythmia is occurring, and, if so, for determining which of the therapeutic functions—pacing, cardioversion, or defibrillation—should be applied at that point in time.

The microprocessor 22 or separate logic 24 in the defibrillator may be used as part of the processing circuitry to calculate the quotient of the standard deviation and the mean of the activity signal, to determine whether that signal is consistent with physiology or is simply a random occurrence, i.e., for discriminating true exercise sensing signals from noise. Random occurrences such as a sudden unsustained movement exhibit a high standard deviation, while the more constant signals associated with true physical activity and exercise display a considerably lower variation from the mean or physiologic statistical norm. This technique may also be used to differentiate different types of physical exercise from one another. Such calculations of standard deviation relative to mean of the signal can be applied as well to signals derived from changes in intrinsic physiological indicators or parameters such as blood temperature detected by the second, complementary sensor 14, for the same purposes.

The capability to differentiate different types of activity from an analysis of the output signal of an exercise responsive (or activity) sensor, such as 30 or 14, may also be used to detect and identify the pattern associated with a particular type of exercise, for comparison with a library of such patterns for recognition and appropriate rate response purposes. On each occasion that the signal falls into a known pattern or template, a particular cardiac response curve can be designated as a pacing rate determinant by means of programming of the implanted device. If a different pattern is exhibited, a different response curve is automatically selected, by virtue of the programming. The curves (algorithms) and the library of patterns can be stored in the memory 23 of defibrillator 10.

After calculating the mean and the standard deviation of the activity signal, the latter is divided by the former, using the processing 31, microprocessor 22, logic 24, and memory 23 of the defibrillator. Large deviations from the mean are discarded as random occurrences, but small deviations are used to differentiate the types of activity engaged in by the patient. Below a predetermined level of deviation at either side of the mean, true physical exercise such as walling or bicycling is indicated, while activity outside that level is of a more random and even spasmodic nature. Within the boundaries of the predetermined level of deviation another boundary or threshold level exists, indicative of bicycling exercise above that level, and indicative of walking exercise below the level.

The sensor output signal may be processed to compare the standard deviation and the mean over time, and a running average of the comparison may then be calculated in blocks of one second each over a substantially longer time interval of several seconds (e.g., 32 seconds) on a first in, first out basis. Signal continuity and consistency over even a relatively brief averaging interval will rule out minor movements and perturbations constituting noise.

The second, complementary sensor 14 detects a parameter complementary to acceleration, such as any of those which have been mentioned above, to provide confirmation or verification of the patient's metabolic state and hemodynamic needs, or to contest the indication provided by the accelerometer 30. A parameter such as central venous blood temperature responds more slowly to the onset of exercise than a pure activity sensor, but can be more specific as to the metabolic level of exercise. The confirmation of activity afforded by the use of a second sensor optimizes control to avoid prolonged false triggerings that might otherwise be encountered.

The complementary sensor serves to limit noise-related false triggerings of a rate increase by a relative change in the signal level of the accelerometer, for example, and the output signal of the accelerometer serves to determine whether an increase in pacing rate is appropriate by virtue of the value of the complementary sensor. If venous blood temperature is the complementary indicator, as in the device of the FIGURE, fever may be detected (or confirmed) in the absence of an activity signal from the accelerometer, to avoid or limit an increase in pacing rate. Absence of motion (detected by the activity sensor) may dictate not only an absolute rate, but a minimum rate determined by the output of the second sensor.

After the physical activity or exercise ends, the pacing rate is preferably decreased to a quiescent base or resting rate under the control of a programmed fall-back or rate-reduction routine, as a function of the corresponding signals from both sensors. In the preceding example, the circumstances indicate that the patient is not undergoing physical activity, so it is appropriate at that point to reduce the stimulation rate toward the base rate. This is useful to distinguish and halt reentry tachycardias in atrial P-wave triggered DDD pacing. A decrease in the pacing rate to the base rate may be inhibited as long as the signal amplitude of the activity sensor exceeds a predetermined level indicative of body activity.

A new baseline or threshold level for activity may be established according to specific inertia criteria of the complementary parameter. If, after a predetermined time interval (e.g., a few minutes), the complementary sensor signal fails to confirm the activity signal of the accelerometer, or vice versa, the current activity signal amplitude may be set as the new baseline value of activity. This serves to avoid a prolonged improper rate increase from false triggering of the activity sensor, even in a noisy environment. The complementary use of two sensors thus provides a more interactive and appropriate rate control.

Processing of the filtered activity signal from accelerometer 30 can be accomplished using an evaluation circuit 32 to process the bandpass signal over successive blocks of time of three seconds each, for example. The difference between maximum and minimum signal amplitudes is calculated for samples taken at predetermined intervals of shorter duration, such as 300 milliseconds each. The calculated amplitude difference is then added to the previous sample for all samples of the first block, and the result is averaged for the first block by dividing by the number of samples taken. If the difference between that average and the average for the second block of time exceeds a predetermined activity baseline, and this is confirmed over the next few blocks of time, it is indicative of activity or of an increase in activity, to establish a new or higher threshold level.

It should now be clear that the invention is of value to avoid shocks to the heart which, while serving to prevent possible sudden cardiac death, can be debilitating and progressively damage the myocardium as well as other tissue of the patient, are unnecessary if the dysrhythmia that prompted them can be prevented by employing a better match between the cardiac pacing function of the medical interventional device and the metabolic and hemodynamic requirements of the patient.

Summarizing the apparatus described above, a defibrillator is adapted to be implanted in the body of a patient, the defibrillator possessing a capability to perform cardiac pacing, cardioversion and defibrillation therapies in selective response to sense signals indicative of respective dysrhythmias of the patient's heart from detection of the patient's cardiac signal. The defibrillator includes a first sensor for sensing the patient's heart rate; and a pulse generator together with a lead-electrode system coupled to detect the patient's heart rate and to deliver cardiac pacing pulses to the patient's heart to correct a dysrhythmia. In its principal aspect, the invention resides in means for optimizing a match between the cardiac pacing rate of the defibrillator and the contemporaneous hemodynamic needs of the implant patient under condition of rest and physical activity. The optimizing means includes means for sensing when the patient is engaging in physical activity and when the patient is at rest, and for generating a signal representative thereof adapted to control the cardiac pacing rate accordingly and, if engaged in activity, according to the extent of the activity. The optimizing means also includes means for processing the control signal generated by the activity sensing means to enhance the sensitivity and specificity of the control signal by distinguishing true physical activity of the patient from false indications of activity and discarding the latter. Further included is means responsive to the processed control signal for application thereof to the pulse generator to control the pacing rate. Thus, the defibrillator is adapted to suppress an acceleration of cardiac dysrhythmias by delivery of pacing therapy that matches the patient's hemodynamic needs, by focusing on correcting cardiac pacing problems before they become sufficiently aggravated to require more aggressive cardioversion and defibrillation therapies. In addition, the sensor controlled rate adaptive function allows for a reduction of pacing rate at resting periods such as at nighttime and thereby saves battery power to increase longevity of the device.

In the preferred embodiment of the defibrillator, the activity sensing means comprises an accelerometer, and the signal processing means includes a low pass filter for passing substantially only components of the control signal in a frequency band below approximately 10 Hz. The filter may perform bandpass filtering in a range between approximately 0.1 Hz and approximately 4.0 Hz. Also, the signal processing means includes means for providing a variable baseline pacing rate to reflect the patient's having commenced different levels of physical activity when and as they occur. Preferably, the accelerometer is mounted within a case that houses electronic circuitry and other components of the defibrillator, and is isolated from pressure exerted external to the case. A second, complementary sensor is electrically coupled to electronic circuitry of the defibrillator for confirmation of the output signal of the accelerometer, the complementary sensor including means for sensing a physiological parameter representative of metabolic and hemodynamic needs of the patient other than physical activity or exercise, preferably selected from the group consisting of body temperature, minute ventilation, Q-T interval, and intracardiac phenomena, In a method implemented by the implanted defibrillator device for performing cardiac pacing, cardioversion and defibrillation therapies in selective response to sense signals indicative of respective dysrhythmias of the patient's heart from detection of the patient's cardiac signal, the patient's heart rate is sensed. If a dysrhythmia is detected, cardiac pacing pulses are delivered to the patient's heart for correcting the dysrhythmia. According to the invention, the correction is performed by optimizing a match between the cardiac pacing rate of the defibrillator and the contemporaneous hemodynamic needs of the implant patient under conditions of rest and physical activity. The optimization is achieved by sensing when the patient is engaging in physical activity and when the patient is at rest, and generating a signal representative of sensed activity and rest to control the cardiac pacing rate accordingly. If the patient is engaged in activity, the control signal is generated also according to the extent of the activity. The control signal is then processed to enhance the sensitivity and specificity thereof by distinguishing true physical activity of the patient from false indications of activity to discard the latter and relay substantially only on the former. The processed control signal is then used to control the pacing rate.

Stated somewhat differently, the apparatus of the invention constitutes an implantable medical interventional device for responding to detection of any of a plurality of cardiac dysrhythmias in a human patient by performing an appropriate therapy including cardiac pacing, cardioversion or defibrillation according to the nature of the detected dysrhythmia. The device includes a first sensor for detecting any of the plurality of cardiac dysrhythmias, and a generator for developing pulses and shocks for delivery to the patient's heart according to whether the detected dysrhythmia is bradycardia or a relatively slow pathologic tachycardia on the one hand, or a relatively fast tachycardia or fibrillation on the other hand. Optimizing means of the device seeks to maintain at all times a substantial match of the patient's heart rate to the normal rate for a healthy person under like conditions of physical exercise, including relatively minor activity, and rest experienced by the patient. The optimizing means includes a second sensor for sensing when the patient is engaged in physical exercise or rest as imposing different hemodynamic demands on the patient's cardiovascular system, and for producing a signal representative of the then-current hemodynamic demand. Here again, signal processing is used to enhance the signal to distinguish components thereof representing true physical exercise by the patient and the extent of such exercise from components of the signal constituting false indications of activity by the patient. The enhanced signal is then applied to the generator to develop pulses for delivery to the patient's heart to vary the heart rate to conform to the then-current hemodynamic demand on the patient attributable to the aforesaid conditions of physical exercise or rest. A third sensor may be used for confirming or contesting the indications of exercise and rest sensed by the second sensor.

Although a best mode currently contemplated for practicing the invention has been described herein, in terms of certain preferred methods and embodiments, it will be recognized by those skilled in the art of the invention that variations and modifications of the disclosed methods and embodiments may be made without departing from the true spirit and scope of the invention. Accordingly, it is intended that the invention shall be limited only by the appended claims and the rules and principles of the applicable law.

What is claimed is:

1. An implantable defibrillator adapted to deliver cardiac pacing, cardioversion and defibrillation therapies in selective response to dysrhythmia detection from an implant patient's cardiac signal, the defibrillator comprising:

a sensor of the patient's heart rate;

a cardioverter/defibrillator for producing electrical shocks of adjustable energy level to be applied to the patient's heart in response to applicable detected levels of pathologic accelerated heart rate;

a rate controllable generator responsive to a pacing dysrhythmia sensed by said heart rate sensor for generating cardiac pacing pulses at a rate designed to correct said sensed dysrhythmia for application to the patient's heart;

an optimizer for matching the cardiac pacing rate of said generator to the hemodynamic needs of the implant patient under conditions of rest and physical activity; including sensing and distinguishing periods of patient physical activity and rest, and generating a signal representative thereof to control the cardiac pacing rate accordingly as well as according to the extent of activity; and a processor for processing the control signal generated by the optimizer to enhance sensitivity and specificity thereof by detecting physical activity of the patient and for applying the enhanced processed control signal to said rate controllable generator to appropriately adjust the pacing rate thereof; said processor including a filter for passing substantially only components of the control signal in a frequency band below approximately 10 Hz;

whereby said defibrillator is adapted to suppress an acceleration of cardiac dysrhythmias by developing and delivering a pacing therapy that matches the patient's hemodynamic needs.

2. The defibrillator of claim 1, wherein said optimizer comprises an accelerometer.

3. The defibrillator of claim 1, wherein said filter performs bandpass filtering in a range between approximately 0.1 Hz and approximately 10.0 Hz.

4. The defibrillator of claim 3, wherein said optimizer comprises an accelerometer.

5. The defibrillator of claim 4, wherein said processor includes means for varying a baseline pacing rate to reflect a changed level of physical activity by the patient, or to reflect periods of patient inactivity with needs for pacing at a rate below a baseline rate.

6. The defibrillator of claim 2, wherein the accelerometer is mounted within a case that houses electronic circuitry and other components of the defibrillator, and is isolated from pressure exerted external to the case.

7. The defibrillator of claim 2, further including a second, complementary sensor electrically coupled to electronic circuitry of the defibrillator for optimizing the output signal of the accelerometer to adapt the pacing rate to the patient's hemodynamic needs more adequately and precisely.

8. The defibrillator of claim 7, wherein the complementary sensor comprises means for sensing a physiological parameter representative of metabolic and hemodynamic needs of the patient other than physical activity, said parameter being selected from the group consisting of body temperature, minute ventilation, Q-T interval, and intracardiac phenomena.

9. An implanted defibrillator device-implemented method of delivering cardiac pacing, cardioversion and defibrillation therapies in selective response to dysrhythmia detection of an implant patient's cardiac signal, said method comprising the steps of:

sensing the patient's heart rate;

delivering cardioversion/defibrillation therapies by producing electrical shocks of adjustable energy level for application to the patient's heart in response to applicable detected levels of pathologic accelerated heart rate; and optimizing a match between the generated cardiac pacing rate and the contemporaneous hemodynamic needs of the implant patient under conditions of rest and physical activity; including sensing periods of patient physical activity and rest and generating a signal representative thereof to control the cardiac pacing rate accordingly and according to the extent of activity by means of an accelerometer mounted onto and integrated within hybrid electronic circuitry.

10. The method of claim 9, wherein the step of activity sensing is performed by an accelerometer constituting one of three types including a piezoelectric type, a piezoresistive type, and a piezocapacitive type.

11. The method of claim 9, wherein the step of signal processing includes filtering said control signal to pass substantially only components thereof in a frequency band below approximately 10 Hz.

12. The method of claim 11, wherein the step of filtering comprises bandpass filtering in a range between approximately 0.1 Hz and approximately 10.0 Hz.

13. The method of claim 9, including optimizing the pacing rate determined from the output signal of the accelerometer with a second, complementary sensor electrically coupled to electronic circuitry of the defibrillator.

14. The method of claim 13, including using the complementary sensor to sense a physiological parameter representative of metabolic and hemodynamic needs of the patient other than physical activity, said parameter being selected from the group consisting of body temperature, minute ventilation, Q-T interval, and intracardiac phenomena.

15. An implantable medical interventional device for responding to detection of any of a plurality of cardiac dysrhythmias in a human patient by performing an appropriate therapy including cardiac pacing, cardioversion or defibrillation according to the nature of the detected dysrhythmia, said device comprising:
  a first sensor for detecting any of said plurality of cardiac dysrhythmias;
  a generator of pacing pulses and electrical shocks for delivery to the patient's heart according to whether a detected dysrhythmia is bradycardia or a relatively slow pathologic tachycardia on the one hand, or a relatively fast tachycardia or fibrillation on the other hand; and
  an optimizer for substantially matching the patient's heart rate to hemodynamic demand under conditions of physical activity and rest of the patient, including:
    a second sensor for sensing periods of patient activity and rest as imposing different hemodynamic demands on the patient's cardiovascular system, and for producing a signal representative of applicable hemodynamic demand, and
    a signal processor for said second sensor signal to detect physical activity of the patient and the extent thereof, and for applying the processed signal to said generator to vary the pacing rate to conform to the patient's hemodynamic demand.

16. The device of claim 15, wherein said second sensor comprises an accelerometer.

17. The device of claim 16, wherein said second sensor detects acceleration in a predominant anterior posterior direction of patient movement.

18. The device of claim 15, wherein said second sensor is mounted in a horizontal axis on said device.

19. The device of claim 15, further including a frequency filter to enhance the specificity of the sensor towards physical exercise.

20. The device of claim 15, further including a third sensor for confirming or contesting the indications of exercise and rest sensed by said second sensor.

21. An implantable defibrillator-implemented method of delivering cardiac pacing, cardioversion and defibrillation therapies in selective response to dysrhythmia detection an implant patient's cardiac signal, said method comprising the steps of:
  sensing the patient's heart rate;
  providing a capability to deliver cardioversion/defibrillation therapies at least partially in the form of electrical shocks of adjustable energy level for application to the patient's heart in response to detected extent of pathologic accelerated heart rate; and
  optimizing a match between a generated cardiac pacing rate and contemporaneous hemodynamic needs of the implant patient by controlling the cardiac pacing rate according to detected conditions of physical activity and rest, including adapting the pacing rate dependent on said detection, and
  further reducing the pacing rate under prolonged conditions of physical rest by the patient.

22. The method of claim 21, including detecting said prolonged conditions of physical rest from a clock function within said defibrillator.

23. The method of claim 21, including detecting said prolonged conditions of physical rest from said detection of conditions of physical activity and rest.

24. The method of claim 21, including detecting said prolonged conditions of physical rest from a combination of a clock function within said defibrillator and said detection of conditions of physical activity and rest.

* * * * *